United States Patent [19]

Sheu et al.

[11] Patent Number: 5,776,108
[45] Date of Patent: Jul. 7, 1998

[54] BLOOD CHECK DEVICE OF AN INFUSION BOTTLE

[76] Inventors: Miin-Tsang Sheu, No. 156, Cheng Kung Road; Yeong-Shing Chern, No. 13, Alley 12, Lane 212, Fu Shan Street, both of Chang Hua City, Taiwan

[21] Appl. No.: 687,175

[22] Filed: Jul. 25, 1996

[51] Int. Cl.$^6$ .................................................. A61M 5/00
[52] U.S. Cl. ........................................ 604/247; 604/257
[58] Field of Search .................................. 137/846, 849; 604/30, 31, 168, 246, 247, 264, 280

[56] References Cited

U.S. PATENT DOCUMENTS

| 4,084,606 | 4/1978  | Mttileman       | 137/102 |
| 4,487,605 | 12/1984 | McGaughey et al.| 604/168 |
| 4,535,819 | 8/1985  | Atkinson et al. | 137/846 |
| 4,612,960 | 9/1986  | Edwards et al.  | 137/846 |
| 5,226,886 | 7/1993  | Skakoon et al.  | 604/153 |
| 5,401,225 | 3/1995  | Sutherland et al.| 604/247 |
| 5,439,451 | 8/1995  | Collinson et al.| 604/247 |

FOREIGN PATENT DOCUMENTS

| 0 139 347 | 5/1984 | European Pat. Off. | 137/846 |

*Primary Examiner*—Michael Powell Buiz
*Assistant Examiner*—Deborah Blyveis
*Attorney, Agent, or Firm*—Beveridge, Degrandi, Weilacher & Young, LLP

[57] ABSTRACT

A blood check device comprises a needle, a barrel connecting the needle, a check tube inserted in the barrel, a sleeve connecting the barrel, and a connecting hose connecting the sleeve. A rear end of the connecting hose connects an infusion bottle. The barrel has a soft pipe and an annular rib disposed in an inner periphery of the soft pipe. An end flange is disposed on a rear open end of the check tube. A tapered notch is formed on a front close end of the check tube. The tapered notch communicates with a hollow interior of the check tube.

5 Claims, 2 Drawing Sheets

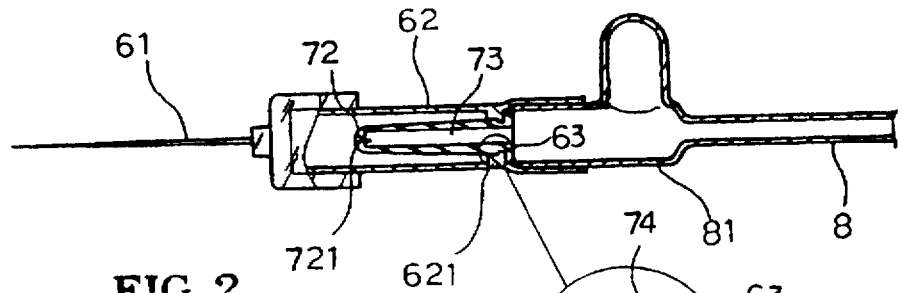
FIG 2
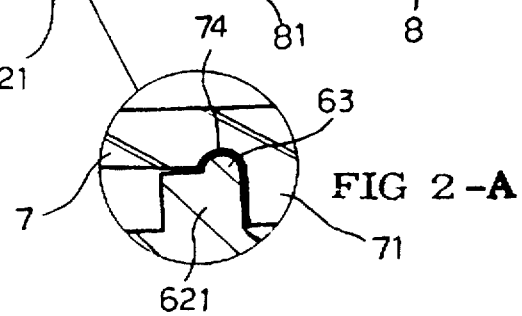
FIG 2-A
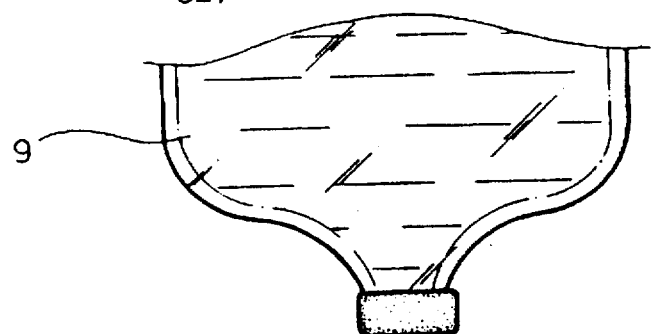
FIG 3-A
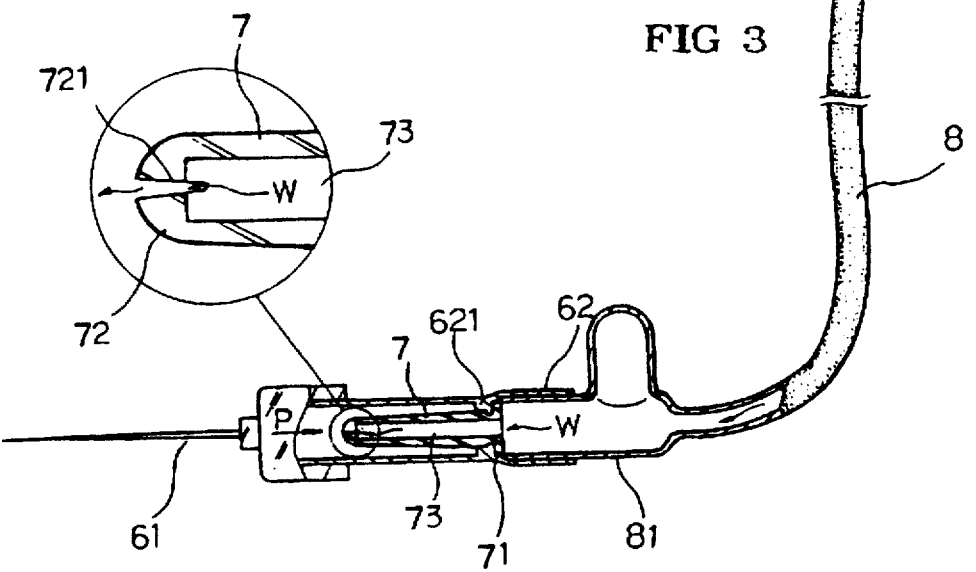
FIG 3

BLOOD CHECK DEVICE OF AN INFUSION BOTTLE

BACKGROUND OF THE INVENTION

The invention relates to a blood check device of an infusion bottle. More particularly, the invention relates to a blood check device which can obstruct the blood of the user flowing into the infusion bottle.

A conventional infusion bottle can contain nutrition liquids. The infusion bottle can contain nutrition liquids with medicines also. The patients may be in a state of malnutrition or undernourishment. The infusion bottle is suitable for intravenous saline infusion or intravenous nutrition infusion. In the total parenteral nutrition, the reverse flow of the blood of the user should be avoided. However, the conventional infusion bottle does not have any blood check device. Thus the blood of the user may enter a hose connecting the needle and the infusion bottle. Now referring to FIG. 4, a conventional blood check device has a first hollow seat 2 and a second hollow seat 3 coupled with the first hollow seat 2. The first hollow seat 2 has a first semi-spherical body 22 and a first sleeve 21 connected to the first semi-spherical body 22. A protruded ring 221 is disposed in an inner periphery of the first semi-spherical body 22 to receive a round valve 222. The first sleeve 21 connects a first connecting pipe 41. The first connecting pipe 41 connects with a barrel 4. The barrel 4 connects with a needle 43. The second hollow seat 3 has a second semi-spherical body 32 and a second sleeve 31 connected the second semi-spherical body 32. A separating plate 33 is disposed in the second semi-spherical body 32. A through hole 331 is formed on the separating plate 33. The second sleeve 31 connects with a second connecting pipe 5. The second connecting pipe 5 connects with a hose of an infusion bottle. However, it is very difficult to form the molds for the first hollow seat 2 and the second hollow seat 3. The first hollow seat 2 and the second hollow seat 3 are generally formed by an injection molding method. In general, the thickness of the first hollow seat 2 and the second hollow seat 3 will not be even. Many injection molding products are produce slightly deformed. Furthermore, the adhesion between the protruded ring 221 and the round valve 222 is not very strong. Thus the protruded ring 221 and the round valve 222 may be easily disconnected. In addition, the pressure of the infusion liquid may influence the flow of the infusion liquid. The flow of the infusion liquid should overcome the blood pressure and the gravity of the round valve 222.

When the pressure of the infusion liquid is decreased, the flow of the infusion liquid may not overcome the blood pressure and the gravity of the round valve 222. Thus the flow of the infusion liquid is unstable.

SUMMARY OF THE INVENTION

An object of the invention is to provide a blood check device which can obstruct the blood of the user from flowing into the infusion bottle.

Accordingly, a blood check device comprises a needle, a barrel connected with connecting the needle, a check tube inserted in the barrel, a sleeve connected with connecting the barrel, and a connecting hose connecting the sleeve. A rear end of the connecting hose connects with an infusion bottle. The barrel has a soft pipe and an annular rib disposed in an inner periphery of the soft pipe. An end flange is disposed on a rear open end of the check tube. A tapered notch is formed on a front close end of the check tube. The tapered notch communicates with a hollow interior of the check tube. The end flange is blocked by the annular rib. A front portion of the sleeve is inserted in a rear portion of the soft pipe. A recessed ring is formed on an outer periphery of the check tube near the end flange. A protruded ring is disposed on the annular rib to engage with the recessed ring. The tapered notch is opened while the liquid pressure in the infusion bottle is larger than the blood pressure. When the infusion liquid is almost gone, the liquid pressure is smaller than the blood pressure. Then the tapered notch is closed.

BRIEF DESCRIPTION OF THE DRAWINGS

FIG. 1A is an enlarged view of a front end of a check tube while a tapered notch is closed;

FIG. 2 is a sectional assembly view of a blood check device of a preferred embodiment in accordance with the invention;

FIG. 2A is a partially enlarged view of a check tube and a barrel;

FIG. 3 is a sectional view illustrating an operation of a blood check device of a preferred embodiment in accordance with the invention;

FIG. 3A is an enlarged view of a front end of a check tube while a tapered notch is opened; and FIG. 4 is a sectional assembly view of a blood check device of the prior art.

DETAILED DESCRIPTION OF THE INVENTION

Figure 1:
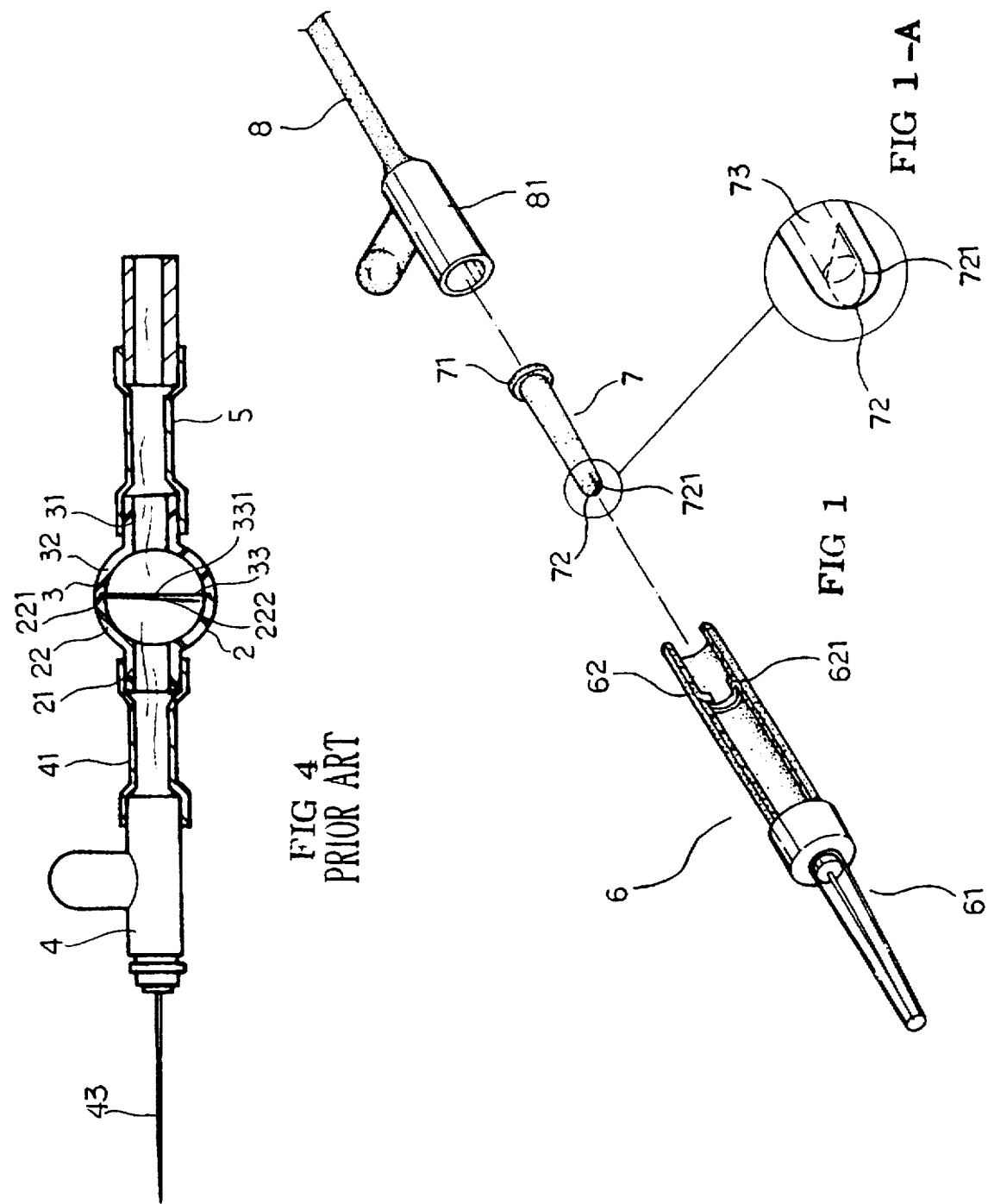
FIG. 1 is a perspective exploded view of a blood check device of a preferred embodiment in accordance with the invention.

Referring to FIGS. 1 to 3, a blood check device comprises a needle 61, a barrel 6 connecting the needle 61, a check tube 7 inserted in the barrel 6, a sleeve 81 connecting the barrel 6, and a connecting hose 8 connecting the sleeve 81. A rear end of the connecting hose 8 connects with an infusion bottle 9. The barrel 6 has a soft pipe 62 and an annular rib 621 disposed in an inner periphery of the soft pipe 62. An end flange 71 is disposed on a rear open end of the check tube 7. A tapered notch 721 is formed on a front close end of the check tube 7. The tapered notch 721 communicates with a hollow interior 73 of the check tube 7.

Referring to FIG. 2A, a recessed ring 74 is formed on an outer periphery of the check tube 7 near the end flange 71. A protruded ring 63 is disposed on the annular rib 621 to engage with the recessed ring 74.

Referring to FIGS. 1 to 3 again, the end flange 71 is blocked by the annular rib 621. A front portion of the sleeve 81 is inserted in a rear portion of the soft pipe 62.

Referring to FIGS. 3 and 3A, the tapered notch 721 is opened while the liquid pressure in the infusion bottle 9 is larger than the blood pressure. When the infusion liquid W is almost gone, the liquid pressure is smaller than the blood pressure. Then the tapered notch 721 is closed. Therefore, the blood of the user will not flow into the barrel 6.

The disadvantages of the conventional blood check device are avoided by the preferred embodiment of the invention.

The invention is not limited to the above embodiment but various modification thereof may be made. Further, various changes in form and detail may be made without departing from the scope of the invention.

We claim:

1. A blood check device, comprising a needle, a barrel engaged with the needle, a check tube having a rear open end and a front end, the check tube being received in the barrel, and a sleeve engaged with the barrel, wherein the barrel includes a pipe member having an annular rib disposed on an inner periphery of the pipe member, the check tube includes an end flange disposed on the rear open end thereof and a tapered notch formed on the front end thereof, the tapered notch communicating with a hollow interior of the check tube, the end flange of the check tube engaging the annular rib of the barrel, and a front portion of the sleeve is received in a rear portion of the pipe member.

2. The blood check device as claimed in claim 1, wherein:

the check tube further includes a recessed ring defined on an outer periphery thereof proximal to the end flange, and the annular rib includes a protruded ring, the annular rib being received, in the recessed ring.

3. The blood check device as claimed in claim 1, wherein:

the pipe member is a soft pipe member.

4. The blood check device as claimed in claim 1, further comprising:

a connecting hose engaged with the sleeve.

5. The blood check device as claimed in claim 4, wherein:

an end of the connecting hose is connected with an infusion bottle.

* * * * *